(12) United States Patent
Boger et al.

(10) Patent No.: US 8,829,074 B2
(45) Date of Patent: *Sep. 9, 2014

(54) BONE CEMENT SYSTEM FOR BONE AUGMENTATION

(71) Applicant: DePuy Synthes Products, LLC, Raynham, MA (US)

(72) Inventors: Andreas Boger, Burgeberbach (DE); Christoph Sattig, Dieburg (DE); Stefan Deusser, Kahl am Main (DE)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/013,327

(22) Filed: Aug. 29, 2013

(65) Prior Publication Data

US 2014/0005635 A1    Jan. 2, 2014

Related U.S. Application Data

(63) Continuation of application No. 13/173,317, filed on Jun. 30, 2011, now Pat. No. 8,546,462, which is a continuation-in-part of application No. PCT/US2011/027142, filed on Mar. 4, 2011.

(60) Provisional application No. 61/310,759, filed on Mar. 5, 2010.

(51) Int. Cl.
*A61F 2/28* (2006.01)
*A61L 24/06* (2006.01)
*A61L 24/02* (2006.01)
*A61B 17/56* (2006.01)
*A61L 27/50* (2006.01)
*A61L 27/46* (2006.01)
*A61L 24/00* (2006.01)
*A61B 17/88* (2006.01)

(52) U.S. Cl.
CPC ............ *A61L 24/0084* (2013.01); *A61L 27/50* (2013.01); *A61L 2430/02* (2013.01); *A61L 27/46* (2013.01); *A61B 17/8805* (2013.01)
USPC ........... 523/116; 523/113; 523/115; 523/117; 623/23.62; 606/94; 604/82

(58) Field of Classification Search
CPC ....... A61K 6/033; A61K 6/043; A61K 6/083; A61K 6/08; A61L 27/46; A61L 27/44; A61L 27/48
USPC ............... 523/116, 113, 115, 117; 623/23.62; 604/82; 606/94
See application file for complete search history.

(56) References Cited

U.S. PATENT DOCUMENTS 4,588,583 A    5/1986   Pietsch et al.
4,902,728 A    2/1990   Pietsch et al.
(Continued)

FOREIGN PATENT DOCUMENTS

EP    0701824    3/1996
EP    1850797    11/2007
(Continued)

OTHER PUBLICATIONS

Baroud et al., "Experimental and theoretical investigation of directional permeability of human vertegral cancellous bone for cement infiltration," J. Biomechanics, Feb. 2004, 37(2), 189-196.

(Continued)

*Primary Examiner* — Michael Pepitone
(74) *Attorney, Agent, or Firm* — Wayne C. Jaeschke, Jr.

(57) ABSTRACT

A bone cement is provided that includes a solid component and a liquid component. The solid component and liquid component are mixed together to form the bone cement. After completion of the solid and liquid component mixing, the bone cement has an initial viscosity effective for manual application or manual injection onto or into a targeted anatomical location, e.g., bone, and the cement has stable viscosity range that over both time and temperature is effective for uniformly filling the targeted anatomical location, for example an osteoporotic bone or a fractured vertebral body, with minimal to no leakage of the cement from the targeted anatomical location. Additionally, both the initial viscosity and the stable viscosity of the bone cement are within a range that renders the bone cement effective for injection with a manually operated syringe or multiple syringes.

25 Claims, 10 Drawing Sheets

(56) References Cited

U.S. PATENT DOCUMENTS

| | | | |
|---|---|---|---|
| 4,910,259 | A | 3/1990 | Kindt-Larsen et al. |
| 5,276,070 | A | 1/1994 | Arroyo |
| 5,650,108 | A | 7/1997 | Nies et al. |
| 5,795,922 | A | 8/1998 | Demian et al. |
| 5,797,873 | A | 8/1998 | Franz et al. |
| 5,902,839 | A | 5/1999 | Lautenschlager et al. |
| 6,020,396 | A | 2/2000 | Jacobs |
| 6,160,033 | A | 12/2000 | Nies |
| 6,752,863 | B2 | 6/2004 | Lyles et al. |
| 6,984,063 | B2 | 1/2006 | Barker et al. |
| 7,014,633 | B2 | 3/2006 | Cragg |
| 7,138,442 | B2 | 11/2006 | Smith et al. |
| 7,160,932 | B2 | 1/2007 | Schilke et al. |
| 2005/0256220 | A1* | 11/2005 | Lavergne et al. ............ 523/115 |
| 2007/0027230 | A1 | 2/2007 | Beyar et al. |
| 2007/0032567 | A1 | 2/2007 | Beyar et al. |

FOREIGN PATENT DOCUMENTS

| | | |
|---|---|---|
| WO | WO 2006/090379 | 8/2006 |
| WO | WO 2008/109045 | 9/2008 |
| WO | WO 2011/028572 | 3/2011 |

OTHER PUBLICATIONS

Baroud et al., "High-Viscosity Cement Significantly Enhances Uniformity of Cement Filling in Vertebroplasty: An Experimental Model and Study on Cement Leakage," SPINE, Oct. 2006, 31(22), 2562-2568.

Hernandez et al., "Influence of Powder Particle Size Distribution on Complex Viscosity and Other Properties of Acrylic Bone Cement for Vertebroplasty and Kyphoplasty," J. Biomed. Mater. Res. Part B: Appl. Biomater., Apr. 2006, 77(1), 98-103.

International Patent Application No. PCT/US2011/027142: International Search Report and Written Opinion dated Jul. 15, 2011, 13 pages.

* cited by examiner

BONE CEMENT SYSTEM FOR BONE AUGMENTATION

CROSS-REFERENCE TO RELATED APPLICATIONS

This application is a continuation of application Ser. No. 13/173,317, filed Jun. 30, 2011, now U.S. Pat. No. 8,546,462, which is a continuation-in-part of PCT Application PCT/US2011/027142 filed Mar. 4, 2011, which claims priority to U.S. Provisional Patent Application Ser. No. 61/310,759, filed Mar. 5, 2010, the disclosures of which are hereby incorporated by reference as if set forth in their entirety herein.

FIELD OF THE DISCLOSURE

The present disclosure generally relates to an improved bone cement composition and a bone cement system for use in bone augmentation. In particular, the present disclosure relates to a bone cement composition having a viscosity range suitable for immediate manual injection. The improved bone cement of the invention also enhances the uniformity of filling and results in reduced leakage flow.

BACKGROUND

Bone cement is conventionally prepared directly prior to injection by mixing a bone cement powder, such as poly-methyl-methacrylate (PMMA), a liquid monomer such as methyl-methacrylate monomer (MMA), an x-ray contrast agent, such as barium sulfate, and an activator of the polymerization reaction, such as N,N-dimethyl-p-toluidine to form a fluid mixture. Other additives including but not limited to stabilizers, drugs, fillers, dyes and fibers may also be included in the bone cement. Since the components react upon mixing, immediately leading to polymerization, the components of bone cement are typically kept separate from each other until the user is ready to form the desired bone cement.

Cement leakage is undesired during vertebroplasty and other similar procedures because it can expose patients to serious risks. Accordingly, the viscosity of the cement is an important factor at reducing unwanted leakage. Concomitant with the use of cements of increasing viscosity, however, is the use of high force injection systems. Such high force injection systems may even exceed human physical limits and preclude important tactile force feedback for the surgeon. High viscosity bone cements also may require longer wait times for the composition to reach sufficient viscosity, thereby reducing total work time. Another possible drawback of high viscosity bone cement may be little interdigitation between cement and bone, thereby compromising the mechanical strength of the reinforced bone.

Other examples of bone cement compositions and/or their uses are discussed in U.S. Pat. Nos. 7,138,442; 7,160,932; 7,014,633; 6,752,863; 6,020,396; 5,902,839; 4,910,259; 5,276,070; 5,795,922; 5,650,108; 6,984,063; 4,588,583; 4,902,728; 5,797,873; 6,160,033; US20070027230; EP1850797 and EP 0 701 824, US Pat. Appln. 2007/0032567.

Percutaneous vertebroplasty is one technique utilizing bone cement for treating weakened or collapsed vertebrae and aids in reducing pain induced by diseases such as osteoporosis. In the vertebroplasty procedure, a fractured vertebral body is augmented with a bone cement. The bone cement polymerizes and hardens upon injection into the vertebral body and stabilizes the fracture. Pain relief for the patient is usually immediate and vertebroplasty procedures are characterized by a high rate of success.

SUMMARY

The present disclosure describes a bone cement formed by a combination of solid and liquid components. The solid component includes a contrast agent, a polymerization initiator, a calcium phosphate based bone substitute material, and a solid polymer, and the liquid component includes a liquid monomer, a polymerization accelerator, and optionally a polymerization inhibitor. According to embodiments of the disclosure, the bone cement has an initial injectable viscosity suitable for manual injection onto or into a targeted anatomical location, where the initial injectable viscosity is formed substantially immediately after combining the solid component and liquid component.

According to one embodiment of the bone cement, the solid component includes the contrast agent at a range of about 38 to about 42 percent by weight of the solid component, the polymerization initiator at a range of about 0.3 to about 0.5 percent by weight of the solid component, the bone substitute material, such as hydroxyapatite, at a range of about 14 to about 16 percent by weight of the solid component, and the solid polymer, which can include one or more of poly(methylacrylate-co-methylmethacrylate), poly(meth)acrylate, polymethyl(meth)acrylate, poly(methylmethacrylate), and/or poly(methylmethacrylate-co-styrene) polymers, blends, mixtures, or copolymers, in the range of about 43 to about 46 percent by weight of the solid component.

According to another embodiment, the bone cement includes the contrast agent, zirconium dioxide, at about 40% by weight of the solid component, the bone substitute material, hydroxyapatite, at about 15 percent by weight of the solid component, and the solid polymer, a mixture of poly(methylacrylate-co-methylmethacrylate) and poly(methylmethacrylate), at about 45 percent by weight of the solid component. According to a further embodiment, the poly(methylmethacrylate) is the range of about 3% to about 15% by weight percent of the solid polymer.

According to one embodiment, the bone cement has a waiting phase of two minutes or less. According to another embodiment, the bone cement has a waiting phase of one minute or less. According to still another embodiment, the bone cement has a waiting phase of substantially zero minutes.

According to one embodiment of the present disclosure, the bone cement, after hardening (or curing), includes the bone substitute material at about 11 percent by weight of the hardened bone cement, the contrast agent at about 29 percent by weight of the hardened bone cement, and, the solid polymer at about 60 percent by weight of the hardened bone cement.

According to a further embodiment, the solid polymer has an average molecular weight range of about 200 kDa to about 1000 kDa. According to a still further embodiment, the solid polymer has an average molecular weight range of about 600 kDa to about 700 kDa. According to yet a further embodiment, the solid polymer has an average molecular weight of substantially 600 kDa. According to another embodiment, the solid polymer includes at least a portion of substantially spherical polymerized beads.

According to one embodiment, the bone substitute material includes sintered hydroxyapatite particles having an average particle diameter range of about 5 um to about 50 um. According to another embodiment, the bone substitute material includes sintered hydroxyapatite particles having an average particle diameter range of about 10 um to about 30 um.

According to one embodiment, the bone cement can include, the contrast agent, zirconium dioxide, at about 40% by weight of the solid component; the polymerization initiator at about 0.4 percent of the solid component; the bone substitute material; hydroxyapatite, at about 15 percent by weight of the solid component; the solid polymer, which can include a mixture of poly(methylacrylate-co-methylmethacrylate) and poly(methylmethacrylate), at about 45 percent by weight of the solid component. The bone cement can further include, the liquid monomer, methylmethacrylate, at about 99.3 percent by weight of the liquid component; the polymerization accelerator, N-N-dimethyl-para-toluidine, at about 0.7 percent by weight of the liquid component; and optionally, the polymerization inhibitor, hydroquinone, at about 60 ppm of the liquid component.

According to some embodiments of the disclosure, the bone cement has an initial injectable viscosity greater than 50 Pa·s. According to another embodiment, the bone cement has a waiting time of less than about 2 minutes. According to a further embodiment, the bone cement has a waiting time of substantially about zero minutes. According to yet another embodiment, the targeted anatomical location is one or more vertebrae. According to still another embodiment, the bone cement, after application, displays minimal leakage from the targeted location.

According to the present disclosure, a bone cement kit for treatment of a targeted anatomical location is disclosed including a first container housing a solid component, including a contrast agent, polymerization initiator, calcium phosphate based bone substitute material, and solid polymer; and, a second container containing a liquid component including a liquid monomer, polymerization accelerator, and optionally polymerization inhibitor. The solid component and liquid component are combinable to form a bone cement having an initial viscosity suitable for manual injection onto or into a targeted anatomical location with minimal leakage. The kit can further include, optionally, one or more syringes adapted to inject the bone cement.

According to further embodiments of the disclosure, a method is disclosed for the preparation of the bone cement according to any of the embodiments of the disclosure. The steps can include:

filling a first container with a solid component including a contrast agent, polymerization initiator, calcium phosphate based bone substitute material, and solid polymer;

filling a second container with a liquid component including a liquid monomer, polymerization accelerator, and optionally polymerization inhibitor; and combining the liquid component and the solid component using a mixer.

According to another embodiment of the present disclosure, a method is disclosed for treating a targeted anatomical location with a bone cement including the step of manually injecting or applying the bone cement according to any of the embodiments of the present disclosure, onto or into the targeted anatomical location. According to a further embodiment, the step of manually injecting includes manual actuation of a first syringe that produces a hydraulic pressure to effect the injection or application of the cement housed in a second syringe.

According to still another embodiment of the present disclosure, a method is disclosed, for augmenting, replacing or treating, weakened or collapsed vertebrae using bone cement. The method can include the step of manually injecting the bone cement according to any of the embodiments of the disclosure, onto or into one or more vertebrae. According to a further embodiment, the step of manually injecting includes manual actuation of a first syringe that produces a hydraulic pressure to effect the injection or application of the cement housed in a second syringe.

Additionally, the bone cement has a viscosity profile over a range of time and temperatures that lengthens the time period during which manual injection can be undertaken. The shortening and/or substantial elimination of a waiting phase due to the relatively high initial injectable viscosity, in combination with the viscosity profile of the cement over a range of time and temperatures, allows a user of the bone cement to prolong the application time, and reduce the leakage profile for injecting the bone cement. Additionally, the initial viscosity and the viscosity profile of the bone cement are within a range that renders the bone cement effective for injection with a manually operated syringe or multiple syringes, rather than a high pressure injection system. This feature is advantageous because high pressure injection systems can lack tactile force feedback.

In addition, the bone cement of the present disclosure provides the benefits of diminished waiting times and increased application times. According to certain embodiments, the bone cement is ready for application or injection immediately upon combination or mixing. Therefore, for such embodiments the waiting time for the bone cement may be shortened to two minutes or less without compromising the safety of the procedure. For other embodiments, the waiting time will be zero minutes as opposed to waiting times for prior art vertebroplasty cements that typically range from 2 to 7 minutes (at around 22° C.). According to some embodiments, the bone cement of the present disclosure can have an application time of at least 15 minutes or more for a temperature range from 19-27° C. as opposed to prior art vertebroplasty cements that typically range from 5 to 12 minutes (at around 22° C.).

BRIEF DESCRIPTION OF THE DRAWINGS

The drawings illustrate generally, by way of example, but not by way of limitation, various embodiments discussed in the present document. The foregoing summary, as well as the following detailed description of preferred embodiments of the application, will be better understood when read in conjunction with the appended drawings.

DETAILED DESCRIPTION

Figure 1:
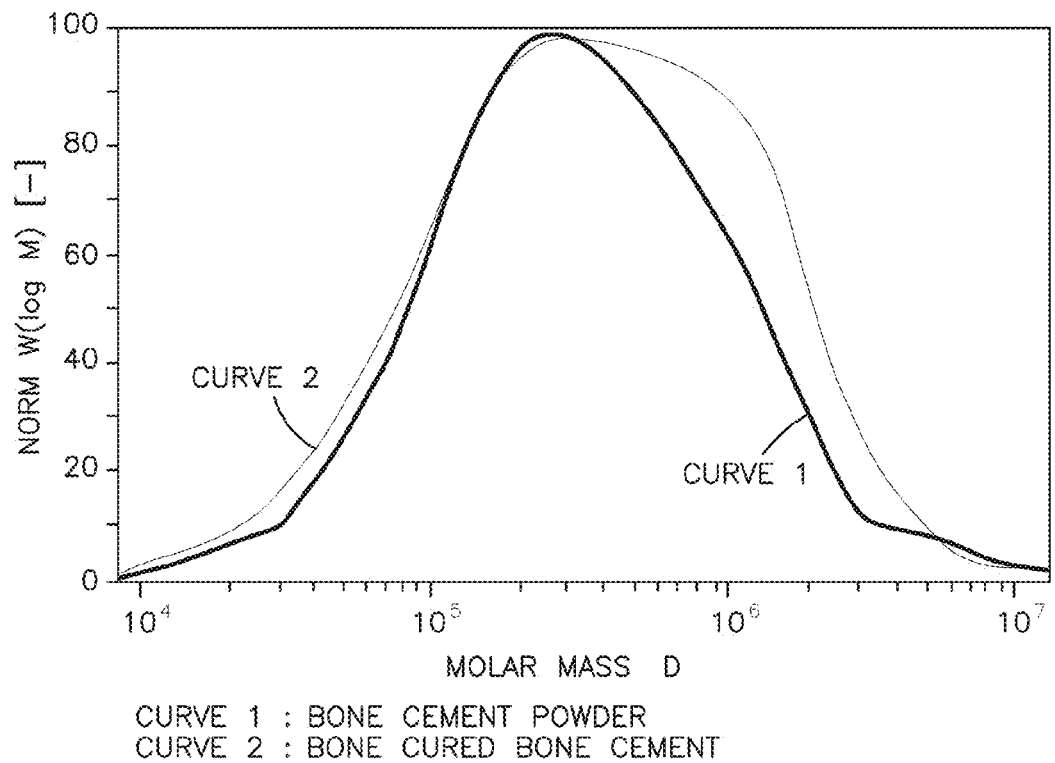
FIG. 1 is a graphical representation of a molecular weight distribution for solid polymer powder component embodiments and for cured bone cement embodiments according to the present disclosure.

In order that the present disclosure may be more fully understood the following definitions are set forth:

The term(s) "waiting phase" or "waiting time" as used herein refer to the time interval after the completion of mixing of the solid and liquid component to form the bone cement, and the bone cement reaching an injectable viscosity level.

The term "injectable viscosity" as used herein refers to a minimum viscosity level suitable for manual application and/or manual injection of the bone cement according to the present disclosure.

The term, "initial viscosity," as used herein, refers to the viscosity measured during the rheological data acquisition in a test known as the Viscosity Measuring Test. Rheological data acquisition was performed as follows: Initial viscosity was derived from rheological investigation of the cement viscosity as a function of time after start of the bone cement preparation. For the viscosity measurements, 3 mL of prepared bone cement were placed in a rotational rheometer (RheolabQC, Anton-Paar, Graz, Austria) with a custom designed double gap measurement system made of PMMA-resistant polypropylene. Real viscosity ($\eta'$) and ambient temperature (T) were recorded directly to a personal computer. The rheometer was set to operate at an oscillatory frequency of 1 Hz and a maximum torque of 3 mN·m. Data was recorded at a frequency of 0.2 Hz. Viscosity measurements were started 2 min. after start of mixing of the solid and liquid components. Rheometer measurements were stopped at a viscosity of 3000 Pa·s. In order to investigate the cement viscosity six trials were performed at each ambient temperature (19, 21, 23, 25 and 27° C., respectively). Temperature was controlled using an air-conditioned lab. Humidity of the lab was controlled and was higher than 40%. Accuracy at ambient temperature was ±0.5 K. Cement viscosity as function of the time after start mixing was presented with one representative measurement for each ambient temperature including standard deviation bars at given cement viscosity levels (50, 200, 500, 1000 and 1500 Pa·s). Initial viscosities for the various ambient temperatures were presented as means and standard deviations (mean±SD).

The term "application time" as used herein, refers to the time interval after the start of mixing of the solid and liquid bone cement components and the bone cement reaching an injection force of 90 N.

The term, "leaked mass of cement," as used herein, refers to the amount of cement that leaks through a leakage model described in 2006 by Baroud et al., "High-Viscosity Cement Significantly Enhances Uniformity of Cement Filling in Vertebroplasty: An Experimental Model and Study on Cement Leakage," SPINE, 31(22), 2562-2568 (2006), hereinafter, "Baroud Model" the disclosure of which is hereby incorporated by reference in its entirety Features of the Baroud Model are also discussed in the following article: Baroud et al., "Experimental and theoretical investigation of directional permeability of human vertebral cancellous bone for cement infiltration," J. Biomech., 37, 189-196, (2004), the disclosure of which is hereby incorporated by reference in its entirety, and are explained further herein.

The term "leakage time" as used herein refers to the amount of time elapsed after start of mixing the solid and liquid bone cement components and the observation of cement leakage that leaks under testing performed according to the Baroud Model as explained further in Example 1.

The term, "injection force," as used herein refers to the Newton's of force required to inject cement into bone under testing known as the Injection Force Measuring Test (the "injection test"). Syringes and injection needles used in the injection test setup were similar to those used in vertebroplasty surgery. One ml syringes (Synthes GmbH) were attached to side opening needles of 8 Ga, 10 Ga and 12 Ga. (Synthes GmbH). The needles presented an inner diameter of 3.2, 2.6 and 1.9 mm, and a length of 176.1, 155.7 and 155.35 mm for the named 8 Ga, 10 Ga and 12 Ga needles, respectively. Those were mounted on an Instron 5866 universal testing machine (Instron, Canton, USA) equipped with a 1.0 kN loadcell to measure injection forces. Injection was performed using a volume flow rate of 0.75 mL/min. Data was recorded at a frequency of 0.2 Hz.

The term, "hardening time," as used herein refers to the time elapsed between mixing the solid and liquid components and hardening or curing of the bone cement.

A bone cement according to the present disclosure is formed from the combining of a solid component (typically constituted in a powder or particle form) and a liquid component that, when combined (e.g., via mixing), form a bone cement having both a relatively high initial viscosity and substantially long application time that is effective for use in manually operated syringe injection systems. The bone cement has an initial injectable viscosity and can be manually injected substantially immediately after completion of mixing, which can limit the waiting phase according to some embodiments to substantially less than two minutes, and according to other embodiments, the waiting phase can be shortened to substantially about zero minutes. Additionally, the bone cement has a viscosity profile over a range of time and temperatures that lengthens the time period during which manual injection can be undertaken. The shortening and/or substantial elimination of a waiting phase due to the relatively high initial injectable viscosity, in combination with the viscosity profile of the cement over a range of time and temperatures, allows a user of the bone cement to lengthen the application time, and reduce the leakage profile for injecting the bone cement for a desired procedure. Such procedures can include for example vertebroplasty, kyphoplasty, and cement augmentation applications The solid component of the bone cement, includes a contrast agent, a bone substitute material and a solid polymer. Suitable contrast agents permit the bone cement to have a radiopacity effective for viewing the bone cement both while it is being injected and once it is injected at a bone site. The radiopacity feature of the bone cement permits the display of any minimal leakage of the cement mixture, once the bone cement mixture is injected into bone using fluoroscopic instruments. Suitable contrast agents can include for example, zirconium dioxide, barium sulfate and/or titanium dioxide and mixtures and blends thereof The contrast agent can be present according to one embodiment in a range of about 30% to about 60% by weight of the solid component; in another embodiment about 35% to about 45% by weight of the solid component; and in still another embodiment about 38% to about 42% by weight of the solid component.

Suitable bone substitute material can include any ceramic composites capable of mimicking the physiological and morphological features of bone, and can include calcium phosphate based compounds, for example, hydroxyapatite $Ca_{10}(PO_4)_6(OH)_2$. According to one embodiment, the bone substitute material is in sintered particle form, for example, sintered hydroxyapatite particles, and can have an average particle diameter range of about 5 um to about 50 um, and preferably from about 10 um to about 30 um. The bone substitute material can be present according to one embodiment in a range of about 0% to about 20% by weight of the solid component; in another embodiment about 12% to about 18% by weight of the solid component; and in still another embodiment about 14% to about 16% by weight of the solid component.

Suitable solid polymer can include (meth)acrylic polymers, for example, polymethyl(meth)acrylate, poly(methylmethacrylate), poly(methylacrylate-co-methylmethacrylate) and/or poly(methylmethacrylate-co-styrene). The solid polymer can include homopolymers and copolymers of the (meth) acrylic polymers as well as mixtures and blends thereof The solid polymer can be present according to one embodiment in a range of about 35% to about 55% by weight of the solid component; and in another embodiment about 43% to about 46% by weight of the solid components. In a preferred embodiment, the solid polymer includes a mixture of the copolymer poly(methylacrylate-co-methylmethacrylate) and the homopolymer poly(methylmethacrylate). In a particularly preferred embodiment, the homopolymer poly(methylmethacrylate) is in a range of about 3% to about 15% by weight of the solid polymer.

The physical and chemical characteristics of the solid polymer portion (typically in a powdered or small particle state) of the solid component can contribute to the relatively high initial injectable viscosity of the bone cement as well as the extended application time according to the present disclosure. These characteristics influence the wetting and swelling behaviors of the bone cement when the solid component is combined with the liquid component to form the bone cement. Such characteristics of the polymer powder particles can include, for example: shape and morphology; surface area and texture; and, average molecular weight range and particle size and distribution. One such example, the variation of the solid polymer particle size distribution to alter the viscosity properties of a cement, is described in Hernandez et al, "Influence of Powder Particle Size Distribution on Complex Viscosity and Other Properties of Acrylic Bone Cement for Vertebroplasty and Kyphoplasty," J. Biomed. Mater. Res.; Part B: Appl. Biomater., 77B(1), 98-103 (2006) (first published online Oct. 20, 2005 at www.interscience.wiley.com), the disclosure of which is hereby incorporated by reference in its entirety. According to one embodiment of the present disclosure, the solid polymer includes polymerized particles having a relatively high surface to volume ratio, preferably substantially spherical beads. Referring to FIG. 1, a molecular weight distribution graph is depicted for the solid polymer of the bone cement (Curve 1) and for the bone cement in its cured or hardened state (Curve 2). According to one embodiment, the solid polymer can have an average molecular weight range of about 200 kDa to 1000 kDa. In a preferred embodiment the average molecular weight range of the solid polymer is about 600 kDa to about 700 kDa, and in a more preferred embodiment, the average molecular weight is substantially about 600 kDa.

The solid component further includes a polymerization initiator, for example, dibenzoylperoxide. The initiator can be present according to one embodiment in a range of about 0.2% to about 0.6% by weight of the solid component; in another embodiment about 0.3% to about 0.5% by weight of the solid component; and in still another embodiment about 0.35% to about 0.45% by weight of the solid component.

According to one embodiment, the bone cement composition includes about 11+/−0.1% by weight of bone substitute material, about 29.3+/−0.1% by weight of a contrast agent and about 59.7+/−0.1% by weight of a solid polymer based upon a weight percentage of the hardened or cured bone cement. According to another embodiment, the solid component of the bone cement includes hydroxyapatite, zirconium dioxide, and a solid polymer.

The liquid component of the bone cement, according to one embodiment can include a polymerization accelerator and a monomer capable of polymerization. The liquid component can further include, according to another embodiment, a polymerization inhibitor that reduces or impedes autopolymerization of the monomer. According to one embodiment, a suitable polymerization accelerator includes N-N-dimethyl-p-toluidin (DMPT). DMPT can be present, according to one embodiment in a range of about 0.4 to about 1.0% by weight of the liquid component; in another embodiment about 0.5% to about 0.9% by weight of the liquid component; and in still another embodiment about 0.6% to about 0.8% by weight of the liquid component. According to one embodiment, a suitable monomer includes methyl methacrylate (MMA). MMA can be present, according to one embodiment in a range of about 99.0% to about 99.8% by weight of the liquid component; in another embodiment about 99.1% to about 99.7% by weight of the liquid component; and in still another embodiment about 99.3% by weight of the liquid component. A suitable polymerization inhibitor includes hydroquinone, according to one embodiment and can be present in a range of about 60 ppm of the liquid component.

According to one embodiment, the bone cement includes a solid component having a solid polymer in a weight percentage of 44.6+/−0.1% of the solid component; a contrast agent in a weight percentage of 40.0+/−0.1% of the solid component; a bone substitute material in a weight percentage 15.0+/−0.1% of the solid component; and a polymerization initiator in a weight percentage of 0.4% of the solid component. According to another embodiment, the bone cement includes a solid component having a copolymer poly(methylacrylate-co-methylmethacrylate) and homopolymer poly (methylmethacrylate) blend as a solid polymer, zirconium dioxide as a contrast agent, hydroxyapatite as a bone substitute material and dibenzoylperoxide as a polymerization initiator.

According to one embodiment, the bone cement has a liquid component having a monomer in a weight percentage of 99.35+/−0.1% of the liquid component; a polymerization accelerator in a weight percentage of 0.65+/−0.1% of the liquid component. According to another embodiment the liquid component is stabilized with about 60 ppm of a polymerization inhibitor. According to a further embodiment, the bone cement has a liquid component having MMA as the monomer, DMPT as the polymerization accelerator, and hydroquinone as the polymerization inhibitor.

According to one embodiment, the bone cement is part of a bone cement application system that also includes a mixer for mixing the powder and liquid. The liquid and solid components of the bone cement are typically separated until intended to be mixed by a technician, doctor or other suitable user. According to one embodiment, the bone cement application system includes a container that contains a pre-filled solid component, the container being sealed with a sterilization cap, and a glass ampoule filled with the liquid component, the ampoule having a crushing ring. The system can further include a transfer cap for transferring the bone cement, after the mixing of the solid and liquid components, to the application system.

Bone cement embodiments described herein are formed by the solid component and liquid component. The solid component and liquid component can be packaged separately, for some embodiments, or together for other embodiments to form a system for manual syringe injection. According to one embodiment manual syringe injection can be accomplished through a system of more than one syringe where manual actuation of one syringe produces a hydraulic pressure to effect the injection of the cement housed in another syringe. According to another embodiment, the manual injection is accomplished directly through manual actuation of a single syringe housing the cement. Once the powder and liquid component are mixed, the bone cement forms. The final cured or hardened bone cement composition includes, for some embodiments, about 11% bone replacement material, about 29.3% of the contrast agent and about 59.7% of the polymer by weight. It should be appreciated that the polymer weight percentage of the cured bone cement includes both the polymer weight percentage of the solid polymer of the solid component as well as the weight percentage of the polymerized liquid monomer of the liquid component.

Figure 2:
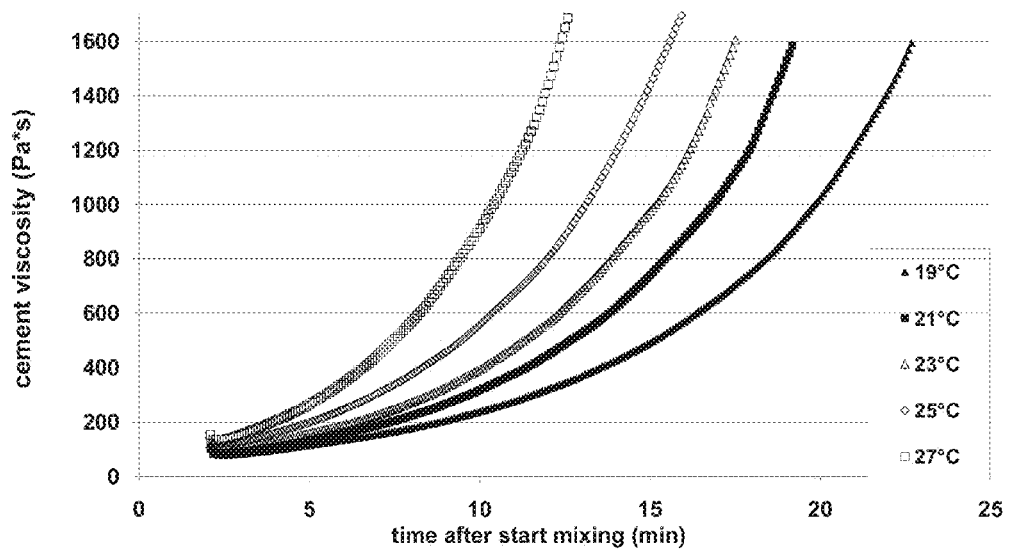
FIG. 2 is a graphical representation of viscosity measurements over time at different ambient temperatures of a bone cement according to some embodiments.
Figure 3:
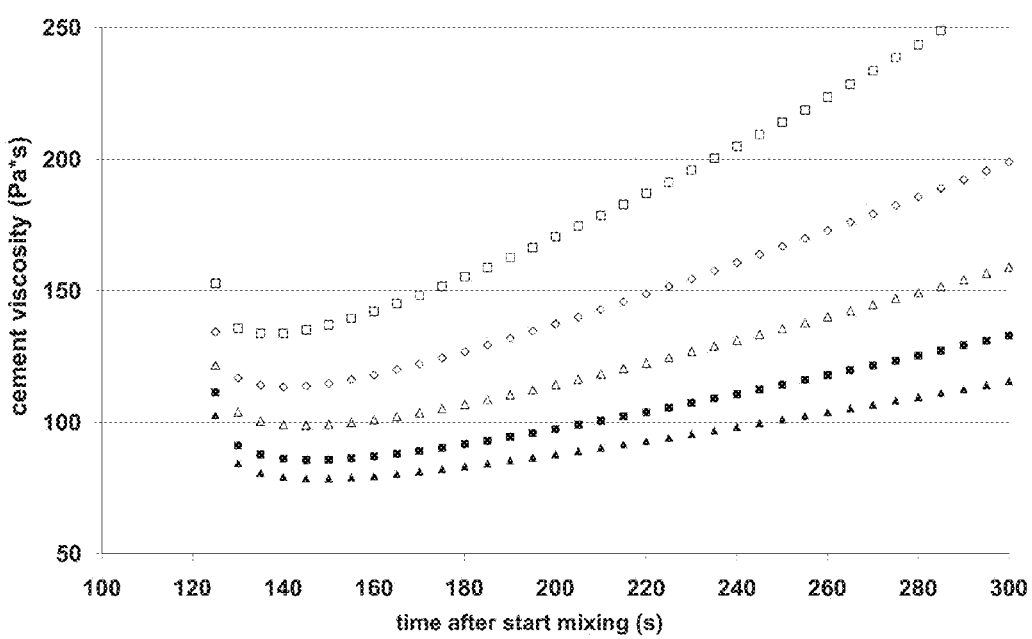
FIG. 3 is a graphical representation of initial viscosity measurements at different ambient temperatures of the bone cement according to some embodiments.

The development of viscosity or a viscosity range, such as initial viscosity, in bone cement is an important factor in working time of the bone cement, the injection force necessary to deliver the bone cement to the targeted anatomical location, the time required for the bone cement to effectively harden or set, and the amount and/or rate of leakage of the bone cement from the targeted location. Viscosity curves for a bone cement according to one embodiment are shown in FIGS. 2 and 3 recorded after the start of mixing of the solid and liquid components at temperatures of 19° C., 21° C., 23° C., 25° C., and 27° C., respectively. The graph shows that the rate of increase in viscosity (measured in Pa·s) is greater at the higher temperatures than at the lower temperatures. At 800 seconds after the start of mixing, the viscosity of the bone cement at 19° C. was about 380 Pa·s. This compares to a viscosity of over 1600 Pa·s at 800 seconds after the start of mixing at temperature of 27° C.

FIG. 3 is a zoom view of FIG. 2 and focuses on the initial viscosity of the bone cement at temperatures of 19° C., 21° C., 23° C., 25° C., and 27° C., respectively, over a time period of 100 to 300 seconds after the start of mixing the solid and liquid components. The rate of increase in initial viscosity is flatter over time across all temperatures than the overall viscosity changes shown in FIG. 2. At 200 seconds from the start of mixing, the initial viscosity of the bone cement was about 70 Pa·s at 19° C., while at 27° C. the initial viscosity was about 170 Pa·s.

FIGS. 2 and 3 illustrate that the initial viscosity of the bone cement maintains stability over a range of temperatures. All initial viscosities shown in FIG. 3 are suitable for injection; i.e., all viscosities shown are initial injectable viscosities. The bone cement has an initial viscosity range between 70-140 Pa·s at all measured temperatures within two minute after mixing has started.

The bone cement system described herein shortens the waiting phase to substantially zero minutes, according to one embodiment, without compromising the safety of the procedure to be performed, for example a vertebroplasty procedure. Additionally, the bone cement can transition to a second stable viscosity that over a range of suitable time and temperature can enable a uniform filling of the targeted anatomical location with minimal or no leakage of the bone cement to adjacent tissue due to the hardening behavior of the bone cement in situ.

Hardening behavior of the bone cement was characterized using rheological measurements, polymerization temperature investigations, injection force measurements, and a hands-on knocking test where the bone cement was tested manually on walnut sized, spherical formed bone cement samples by knocking them on the table. Because the temperature influences the hardening behavior enormously (hardening rates increase with increasing temperature), hardening behavior was investigated at different ambient temperatures, as well as at 37° C. to simulate body temperature. According to one embodiment, the hardened or cured bone cement can have a glass transition temperature range of about 100° C. to about 125° C.

The injection test was performed as follows: After cement preparation, the cement was filled in ten 1 ml syringes. A first syringe was mounted on the injection needle. Injection was started with a delay of 5 min and 10 min after the start of mixing for the tests performed at ambient temperature of 23, 25, 27° C. and 19, 21° C., respectively. Injection was performed using volume flow rate of 0.75 mL/min (stepwise injection) followed by the injection of the other syringes until an injection force of 150 N was recorded due to the polymerization and hardening of the cement sample. The flow rate was chosen at the lowest limit of average clinical measurements, and the hardening time was determined as the time elapsed after the start of mixing and the cement reaching a hardened state.

Figure 4:
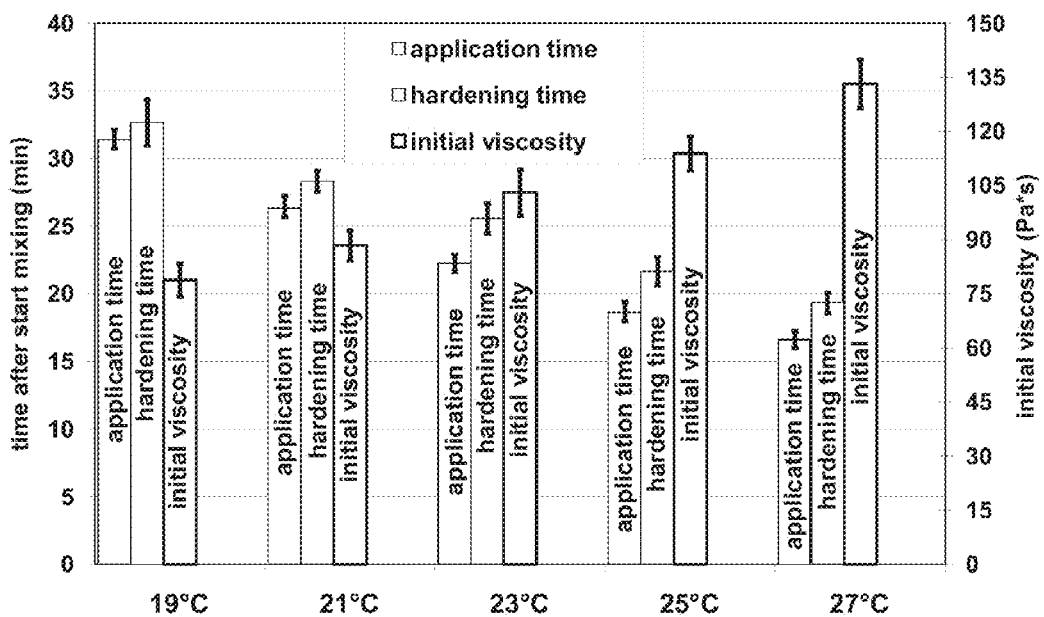
FIG. 4 is a graphical representation of application time, hardening time and initial viscosity at different ambient temperatures of the bone cement, according to some embodiments.

FIG. 4 illustrates that hardening time decreases with increasing temperature, from about 33 minutes from the initiating of mixing at 19° C., to about 19 minutes from the initiating of mixing at 27° C. Application time also decreases with temperature, from about 31 minutes from the initiating of mixing at 19° C., to about 17 minutes from the start of mixing at 27° C. These times and temperatures fall within acceptable ranges for performing the vertebroplasty procedure.

Figure 5:
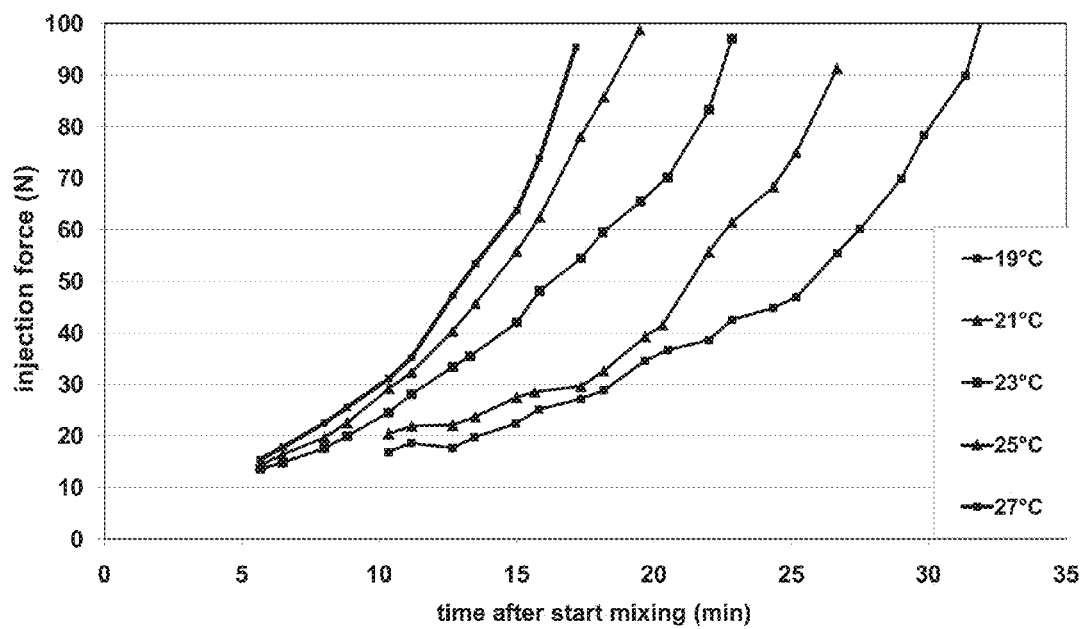
FIG. 5 is a graphical representation of injection force curves for injecting the bone cement at different ambient temperatures according to some embodiments.

Injection force required to move the bone cement into bone increases with increasing temperature, as shown in FIG. 5. For example, at 15 minutes after start mixing the injection force at 19° C. is about 21 N, while the injection force at 27°

C. is about 60 N. The rate of increase of injection force is greater for cement mixtures at 27° C., than at 19° C. These injection forces are within a range wherein hand-operated syringes are usable.

Figure 6:
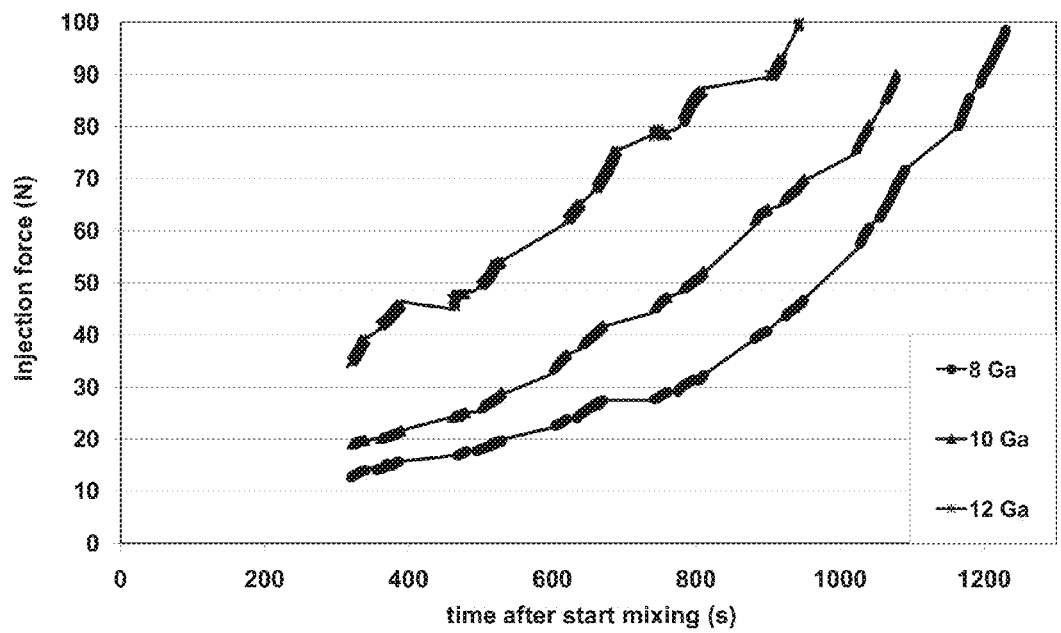
FIG. 6 is a graphical representation of injection force curves for injecting the bone cement using various gauged needles according to some embodiments.

In addition to temperature, adjustment in the size of needle gauge used to inject the bone cement in bone has an impact injection force over time, as shown in FIG. 6. The data displayed in FIG. 6 was obtained at room temperature. The data shows that the injection force increases over time as the gauge of the syringe increases from 8 to 10 to 12 gauge (i.e., as syringe diameter decreases). Specifically, FIG. 6 shows that the injection force was about 30 N for the 8 gauge and about 80 N for the 12 gauge at 800 seconds after the start of mixing the solid component and liquid component. The rate of increase of injection force over time is faster for the higher gauge needle than for the lower gauge needle. The test results obtained for the injection force ranges are all within a range that permits a use of manually operated syringes to inject the bone cement to a targeted anatomical location, e.g., a vertebral body.

Figure 7:
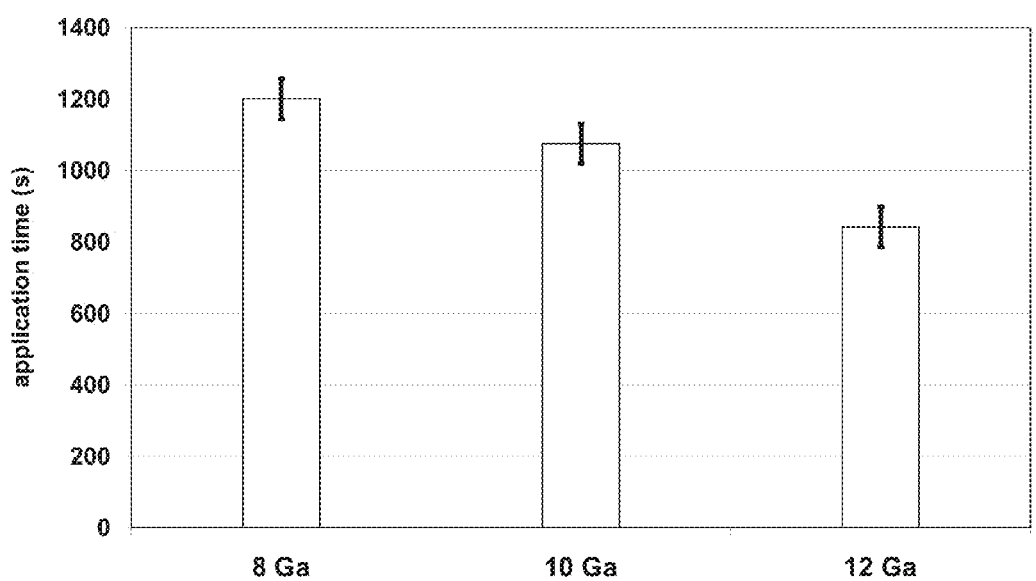
FIG. 7 is a graphical representation of application times for applying the bone cement using various gauged needles, according to some embodiments.

FIG. 7 shows that application time decreases with an increase in gauge number. Specifically, the application time for an 8 gauge needle is about 1200 seconds and the application time for a 12 gauge needle is about 820 seconds.

The bone cement described herein reduces the waiting phase or waiting time for injection; that is, the bone cement as described herein reaches an initial injectable viscosity at or near the completion of mixing of the solid and liquid components. Additionally the bone cement provides sufficient application time to complete the desired procedure, e.g., a vertebroplasty. Furthermore, the bone cement has a range of injection forces over time, temperature and syringe gauge size that enables it to be usable in syringe systems. These properties allow a surgeon to begin injection immediately after cement preparation and to continue the procedure without waiting for the cement to reach a minimum initial viscosity level or rushing a procedure due to a shortened application time because of a concern that the bone cement will reach a viscosity level that is too high to remain workable.

Figure 8A:
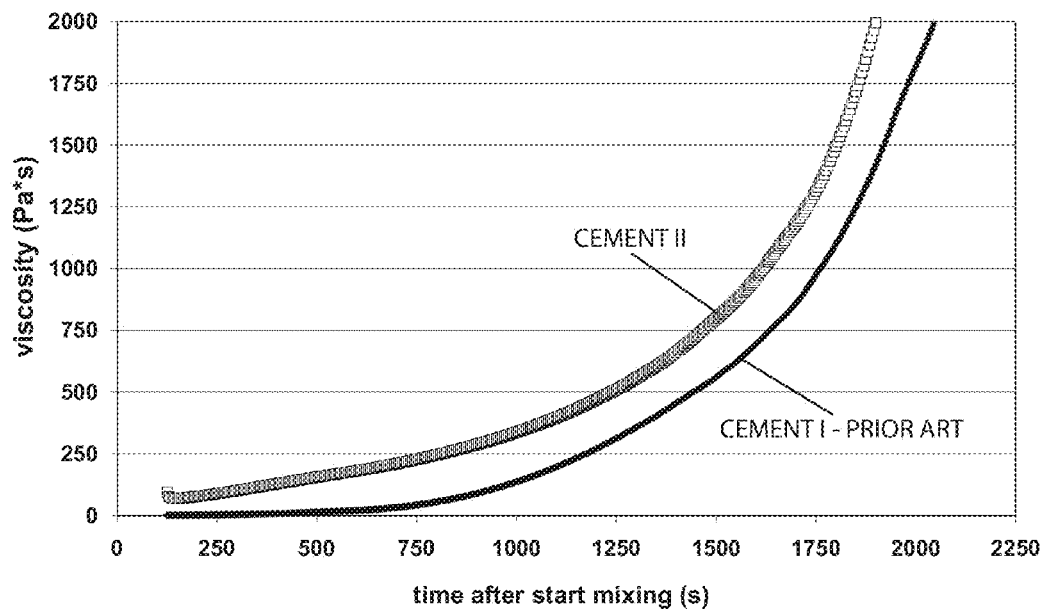
FIG. 8A is a graphical representation of viscosity measurements of two bone cements as a function of time after mixing (Cement I: bone cement formulation according to prior art; Cement II: bone cement formulation according to an embodiment of the present disclosure.
Figure 8B:
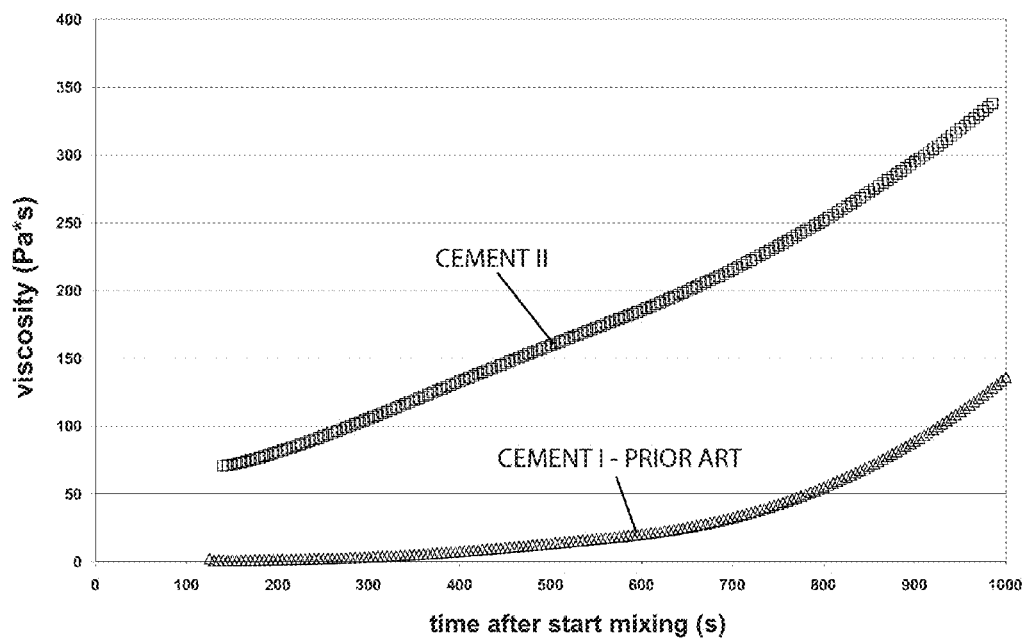
FIG. 8B is a graphical representation of initial viscosity measurements of the bone cements, Cement I and Cement II of FIG. 9A.

Viscosity measurements for an embodiment of the bone cement as described herein (designated "Cement II), are shown in FIGS. 8A and 8B in comparison to a prior art bone cement formulation (designated "Cement I). As can be seen in FIG. 8B, Cement II has an initial injectable viscosity, while Cement I does not. Cement I also displayed leakage in the Baroud Model (discussed further below) when the cement was injected at an initial viscosity of 10 Pa·s, which was the initial viscosity of Cement I immediately following the completion of mixing the components of Cement I. Reduction in the degree of leakage of Cement I can only be accomplished through a delay in the injection, i.e., with a waiting phase after the completion of mixing the prior art bone cement. This waiting phase allows Cement I to increase viscosity to a higher level that is suitable for injection. Cement II displayed minimal leakage when injected immediately after mixing the solid and liquid components; i.e., Cement II was not limited with a waiting phase after completion of the mixing of the solid and liquid components.

A higher uniformity of cement filling and reduced cement leakage was obtained for Cement II compared to a range of tested viscosities of Cement I as explained in detail below in Example 1. Cement II shortens the waiting time or waiting phase to reaching an initial injectable viscosity to at least less than one minute according to some embodiments of the present disclosure, and in other embodiments, Cement II can have an initial injectable viscosity substantially immediately after mixing is completed. Additionally, the viscosity range of Cement II has a second stable viscosity to allow a sufficient application time to complete the desired procedure with a minimal leakage profile.

EXAMPLES

Examples are provided below to illustrate embodiments of the present invention. These examples are not meant to constrain the present invention to any particular application or theory of operation.

Example 1

A study of cement leakage and cement filling performance was performed using one embodiment of the present disclosure described herein, Cement II, and a prior art cement, Cement I. Cement I is a prior art vertebroplasty cement having a low initial viscosity after preparation. In particular, Cement I is a prior art, vertebroplasty cement, identified as Vertecem Mixing Kit, Ref 07.702.010, LOT 043R/0834, Synthes GmbH, Oberdorf, Switzerland. Cement II included a solid component and a liquid component. The solid component included a solid polymer in a concentration of 44.6% by weight of the solid component, having at least the copolymer poly(methylacrylate-co-methylmethacrylate); a contrast agent, zirconium dioxide in a concentration of 40.0% by weight of the solid component; a bone substitute material, hydroxyapatite in a concentration of 15.0% by weight of the solid component; and a polymerization initiator, dibenzoylperoxide (100%) in a concentration of 0.4% by weight of the solid component. The total weight of the solid component was 26.0 grams. The liquid component includes a monomer, methylmethacrylate, stabilized with 60 ppm of polymerization inhibitor, hydroquinone in a mass of 99.35%. The liquid component also includes a polymerization accelerator dimethyl-para-toluidine of 0.65% by mass for a total volume of 10.00 ml. The liquid and solid components were contained separately and were mixed on-site.

The study was performed using the Baroud Model described in 2006 by Baroud et al., "High-Viscosity Cement Significantly Enhances Uniformity of Cement Filling in Vertebroplasty: An Experimental Model and Study on Cement Leakage," SPINE, vol. 31, No. 22, pp. 2562-2568 (2006), and Baroud et al., "Experimental and theoretical investigation of directional permeability of human vertebral cancellous bone for cement infiltration," J. Biomechanics, 37 (2004), pp. 189-196. The Baroud Model measures leakage phenomenon in vertebral body augmentation by artificially creating a path that simulates a vertebral blood vessel to facilitate and favor the forces underlying intravertebral cement flow and to provoke cement leakage. The Baroud Model was utilized to estimate both the leakage and filling behavior of the two vertebroplasty cements, Cement I and Cement II, and reduce the risk of leakage by identifying the conditions for uniform cement filling.

To perform the Baroud Model testing, cylindrical porous aluminum foams (ERC Aluminum and Aerospace, Calif.) were custom made to exhibit geometric, morphologic, and flow properties similar to those of vertebral bone. This aluminum foam was selected because of a well-connected, controlled porosity.

Figure 9A:
FIG. 9A is a perspective view of a micro-computed tomography image of osteoporotic cancellous bone.
Figure 9B:
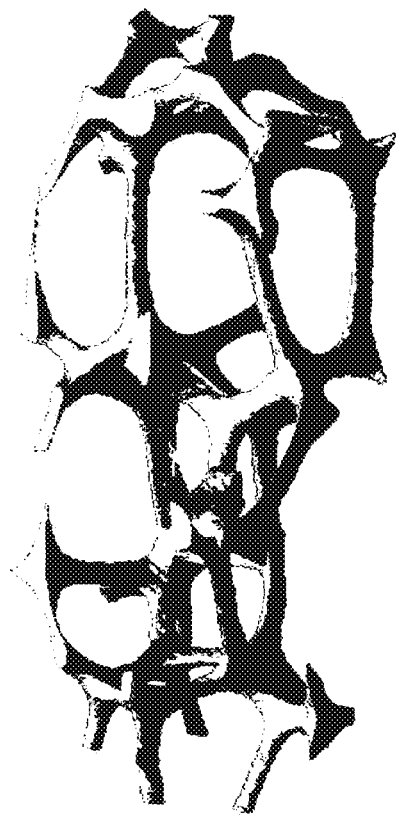
FIG. 9B is a perspective view of a micro-computed tomography of a cancellous bone substitute.

To ensure that the aluminum foam samples (hereinafter "porous substitute samples") had similar morphologic and flow features to those of cadaveric cancellous bone tissue, the following steps were undertaken. The porosity of three porous substitute samples was measured, using non-invasive microcomputer tomography (MicroCT), and Archimedes submersion experiments. The porosity was found to be 91.1%+/−0.6%. Porosity is a measurement of the void volume of a sample, therefore, approximately 9% of the sample is composed of aluminum, the other 91% was void. This value is relatively consistent with the porosity values of osteoporotic cancellous bone that had been excised from the vertebral bodies in previous studies. In healthy bone, the porosity can be as low as 75% and in osteoporotic bone as high as 95%. The remainder of the bone is typically filled with bone marrow, fat, and blood. FIGS. 9A and 9B are representative Micro CT images of the morphologic features of both a bone sample and a porous substitute sample, respectively, highlighting the porosity and well-connected cavities.

In addition to the porosity measurements, the permeability of porous substitute samples was measured using Darcy's flow protocol and was compared to the permeability of cancellous bone. In these flow protocols, constant flow was established through the porous substitute samples, and the pressure drop in the through flow was measured.

The diameter and height of the porous substitute samples were 38.1 and 25.4 mm, respectively. These dimensions were chosen to represent a thoracolumbar vertebra, where most vertebral fractures occur. Therefore, the Baroud Model is representative in terms of geometry, as well as porosity and permeability.

Figure 10:
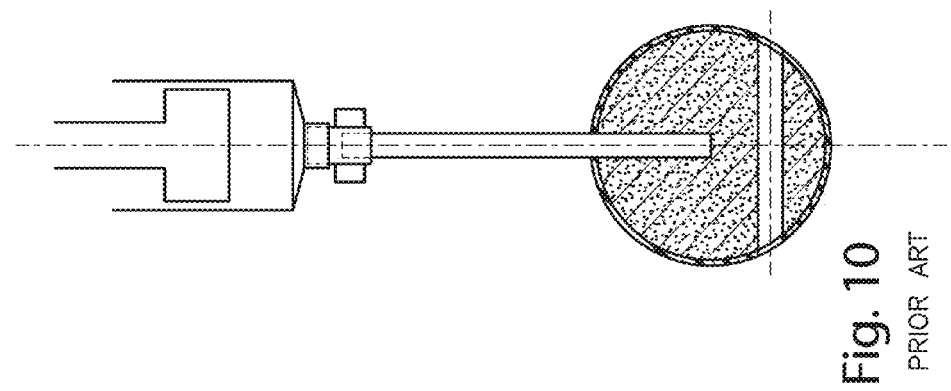
FIG. 10 is a schematic view of a porous bone substitute sample prepared according the Baroud Model discussed herein.

A 3 mm cylindrical channel (mimicking an intravertebral blood vessel) was drilled in the main plane of the porous substitute samples to form a leakage path. To permit insertion of the bone cement injection cannula, a cylindrical channel with a diameter of 4.1 mm was drilled perpendicular to the leakage path, as shown in FIG. 10. The diameter of this injection channel matches the outer diameter of an 8-gauge cannula, which is representative of the gauge used to perform a vertebroplasty procedure.

After creating the leakage path and the injection channel, each porous substitute sample was placed in a bath filled with a water/gelatin solution (Kraft Canada, Inc., Don Mills, Ontario) at room temperature, according to the manufacturer's instructions (5% gelatin by mass). The bath was then placed overnight in a refrigerator at 4° C. to allow the solution to gel, after which the gelatin remained in the porous substitute sample, simulating the presence of bone marrow.

The point in time at which bone cement leakage was observed from the leakage path was recorded using a stopwatch that was started at the start time of mixing the solid and liquid components. The injection pressure was measured with the load cell of the materials testing system.

The cement that leaked through both openings of the leakage path, i.e., the leaked mass, was collected in aluminum weighing cups (Fisher Scientific International, Inc. Hampton, N.H.). Boiling water dissolved the gelatinous material, and, thereafter, a 2.5 micron filter (Whatman, Middlesex, UK) was used separate the cement from the solution. After drying the filter paper in a fume hood, the mean mass of cement that had leaked was determined by taking the average of the cement collected from both openings of the leakage path.

An important addition to the experimental protocol of Baroud Model was that the porous substitute samples were placed in a water bath at 37±1° C., simulating human body temperature. Because the nature of the polymerization reaction that forms the bone cement is a radical reaction, it is accelerated at higher temperatures. In the human body, at a temperature of 37° C., the bone cement cured faster than in ambient temperature.

Materials used in the Baroud Model were similar to those used in vertebroplasty surgery and include bone cement, syringes, needles and viscometer for viscosity control.

Six experimental groups were evaluated. Five groups used Cement I, having a range of initial viscosities at injection. The sixth group included Cement II, starting injection immediately subsequent to cement preparation.

In order to perform the experiment using a 37° C. water bath, a form-stable bone marrow simulant at 37° C. was prepared. The following steps were followed to prepare a starch mixture which is stable at 37° C. as a bone marrow substitute: Cornstarch powder (MAIZENA®, Knorr AG, Thayngen, Switzerland) and cold water were mixed by a ratio of 1:3 by stirring thoroughly at room temperature until a uniform and homogeneous milk-like appearance was achieved.

Next, the porous substitute samples were soaked into the starch mixture and the mixture was heated using medium heat while stirring constantly in the same direction. The mixture was stirred and heated until it thickened and boiled. Then stirring was stopped and the mixture was left on heat for 1-2 minutes before heating was stopped and the porous substitute samples were removed. After the mixture cooled, the porous substitute samples were placed in a refrigerator for 1 hour. Each sample was weighed before and after being filled with the starch mixture, assuring that at least 95% of the voids of the porous substitute samples were filled. The final preparation step of the Baroud model included attaching a thin layer of around 3 mm in thickness of acrylic cement (DP-Pour, DenPlus Inc., Montreal, QC) to give the model a hard shell. This thin layer was intended to act as a simulation of the cortical shell of the vertebral body.

In order to investigate the leakage behavior for Cement I and Cement II, an 8 gauge syringe with a length of 150 mm was inserted into the injection channel of the porous substitute sample according to the Baroud Model. The porous substitute samples, filled with the starch solution, were place into a 37° C. water bath (simulating human body temperature) to reach thermal equilibrium approximately 30 minutes prior to bone cement injection.

Cement I and Cement II were each prepared according to the manufacturer's instructions using a closed mixing device. The time after starting mixing was recorded using a stopwatch, started at the same moment as adding the liquid component to the solid component. A total of 9 ml of the prepared cement was transferred using a luer-luer coupling adapter into three 3 ml syringes (Viscosafe Injection Kit, Ref 07.702.210, Synthes GmbH, Oberdorf, Switzerland) for injection and viscosity measurement. The first two syringes for each bone cement sample were used for injection into the porous substitute sample, and a third syringe was submitted for viscosity measurement using a viscometer (Viscosafe Viscometer, Anton Paar, Graz, Austria, SN 80215110 REF 03.702.010) which was kept at 22±1° C. The viscometer records real viscosity every 5 s directly to a PC using the corresponding software (RHEOPLUS/32 Multi 128 V2.66, Anton Paar, Graz, Austria).

To perform the injection tests, a 3 ml syringe filled with cement was attached to the 8 gauge needles and mounted on a universal testing machine (MTS Mini Bionics 858, MTS, 14000 Technology Drive Eden Prairie, Minn., USA 55344). The starting points of cement injection into the porous substitute samples was determined by reaching a predefined viscosity threshold as measured in real-time by the viscometer. Predefined viscosities for start injection for Cement I were 10, 50, 100, 200 and 400 Pa·s, respectively. A total of 6 ml of each of the Cement I samples was injected using a two-step injection of two 3 ml syringes. The injection rate was 3.5 ml/min.

Cement II was injected directly after transferring the cement to the syringes and mounting on the testing machine.

Injection was started 3 min after the start of mixing, using a cross head speed of 3.5 ml/mm. For all cement groups, the time elapsed for changing from the first to the second syringe was 90 s.

During cement injection each of the porous substitute samples was observed for cement leakage from both sides of the leakage channel and the leakage time was recorded. After the entire cement injection procedure ended, the leaked cement from each sample was collected and weighed, defining the leaked mass. Afterwards, each porous substitute sample (now filled with bone cement) was removed from the water bath and left at room temperature for 2 days to assure that the cement was totally cured. For the five groups using Cement I, five repeats were done. Seven repeats were performed using Cement II.

To evaluate the filling pattern of the bone cement in each of the porous substitute samples, each sample was cut normal to the axis along the injection pathway, into two halves, using a water-cooled diamond saw. Then each half was washed with hot water to dissolve the starch solution. For both halves of the same sample, images were taken, digitized and analyzed for eccentricity and averaged for the same samples as described in Baroud Model. Briefly, eccentricity is defined as the eccentricity of an ellipse having the same second moment of area as the filled configuration. The more uniform and circular the filled pattern is, the less the eccentricity value will be. For example, in a straight line the eccentricity is one, and for a circle it is zero.

The measured endpoints were the eccentricity and the mass of leaked cement collected from the water bath at the end of each experiment. The influence of the material composition of Cement II and of the initial viscosity values of Cement I (fixed independent factors) on the leaked mass and eccentricity (dependent parameters) were statistically analyzed. Overall statistical analysis on the resulting six material groups was performed using univariate ANOVA. Because of the significant differences received from ANOVA ($p<0.006$), multiple post hoc comparisons were done by performing Tukey HSD test. In all cases, a p-value of $\leq 0.05$ was used as significance limit. Statistical analyses were performed using SPSS software version 15.0. The observed leakage profiles of the tested porous substitute samples are illustrated in FIGS. 13A-F. FIGS. 13A-E illustrate the Cement I cross-sections at a start injection viscosity of 10 Pa·s, 50 Pa·s and 100 Pa·s, 200 Pa·s and 400 Pa·s, respectively. FIG. 13 F illustrates the Cement II cross-section injected substantially immediately after mixing.

Figure 11:
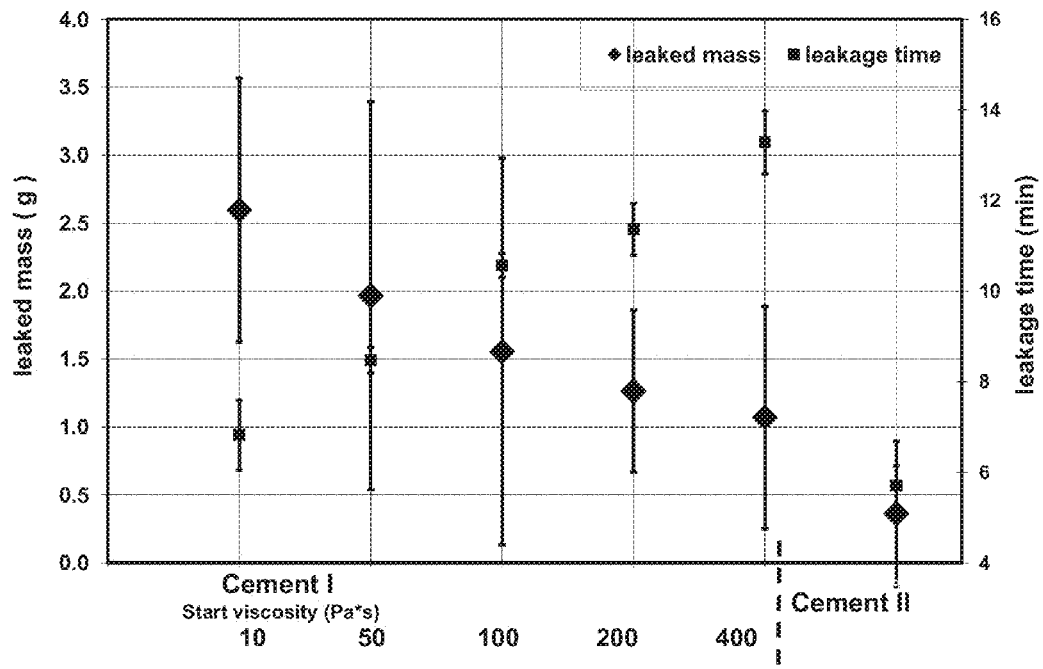
FIG. 11 is a graphical representation of leaked mass and leakage time of Cement I and Cement II according to the Baroud Model discussed herein.

FIG. 11 graphically illustrates leaked mass as a function of starting viscosity. Qualitatively, high leakage mass was observed for Cement I when injected at low viscosity levels (e.g. 10 Pa·s). The values shown in FIG. 10 correspond to the filling patterns observed for the corresponding Cement I samples in FIGS. 13A-E. A more uniform filling could be obtained using higher injection viscosities up to 400 Pa·s for Cement I.

As received from ANOVA testing, the leaked mass in the Cement I groups decreased with the increase of the starting viscosity from 10 to 400 Pa·s. 2.56±0.98 g of Cement I leaked when the cement was injected at an initial viscosity of 10 Pa·s. Delaying the injection of Cement I, i.e., increasing the waiting phase after mixing, resulted in an increased starting viscosity and a corresponding reduction of the leaked cement mass. When injected at an initial viscosity of 400 Pa·s, only 1.07±0.82 g of Cement I leaked.

For Cement II, no waiting phase was required and only minimal leakage was observed. More specifically, the average leaked amount was 0.36±0.54 g and the absolute leaked mass was below 1 g for all tests performed. Furthermore, of the seven leakage models injected with Cement II, there have been three observations without leakage.

Due to the high scattering of the data, especially the data received from the Cement I groups, statistical difference was low in general. Significant differences in leaked mass could be obtained between Cement I group injected at 10 Pa·s and the Cement II group injected directly after mixing ($p=0.003$), shown in FIG. 10. With a p-value of 0.084 (0.173) the difference between the Cement I groups 10 Pa·s through to 400 Pa·s, the leaked mass showed a clear trend in reduced leakage for higher injection viscosity. Comparing the Cement I group injected at 50 Pa·s and Cement II showed also a clear trend in reduced leakage rate using Cement II with a p-value of 0.061. All other pairs yield no significant results presenting p-values higher than 0.275.

Figure 12:
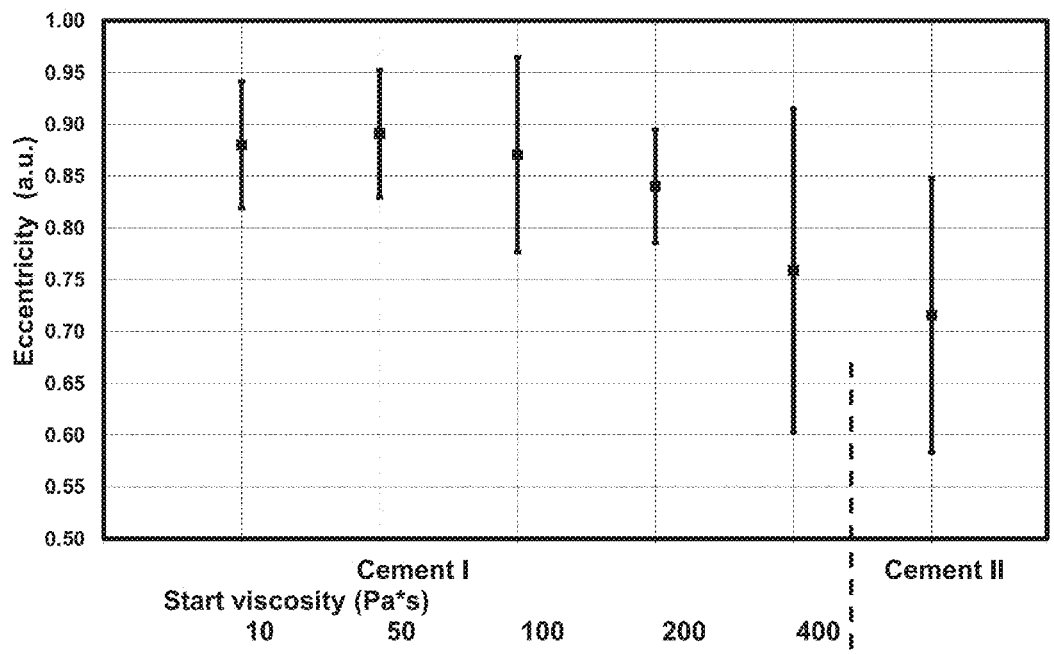
FIG. 12 is a graphical representation of the average filling pattern of Cement I and Cement II, according to the Baroud Model discussed herein.
Figure 13A:
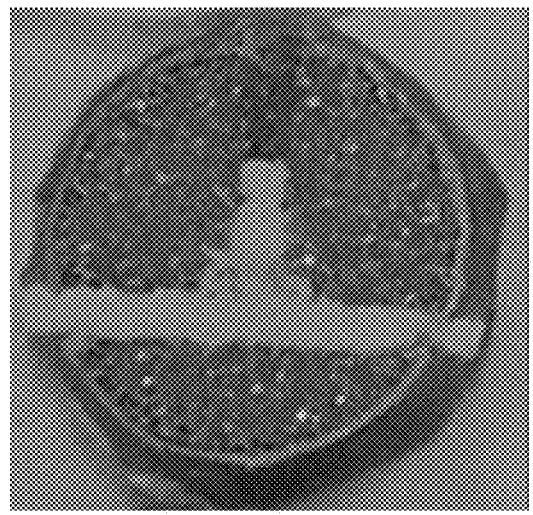
FIGS. 13A-E, are cross-sectional views of porous substitute samples tested under the Baroud Model for Cement I over a range of initial injection viscosities.
Figure 13B:
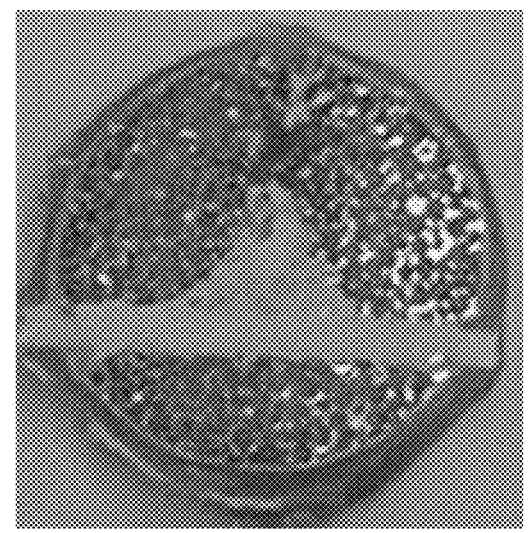
Figure 13C:
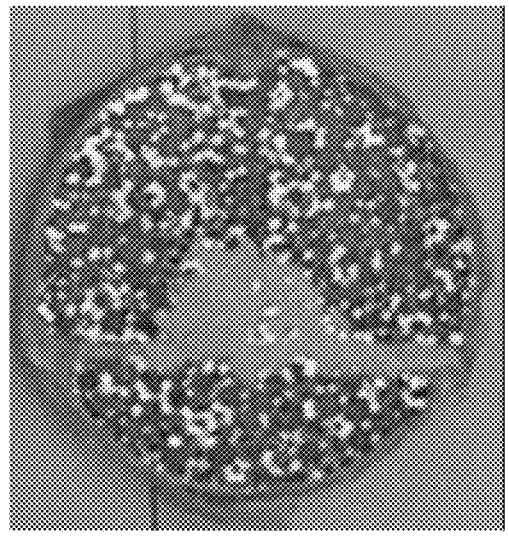
Figure 13D:
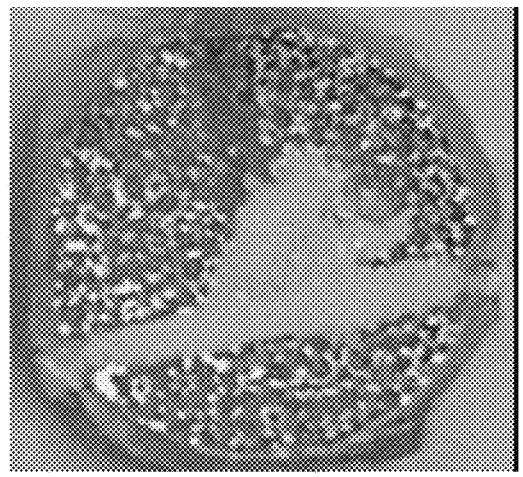
Figure 13E:
Figure 13F:
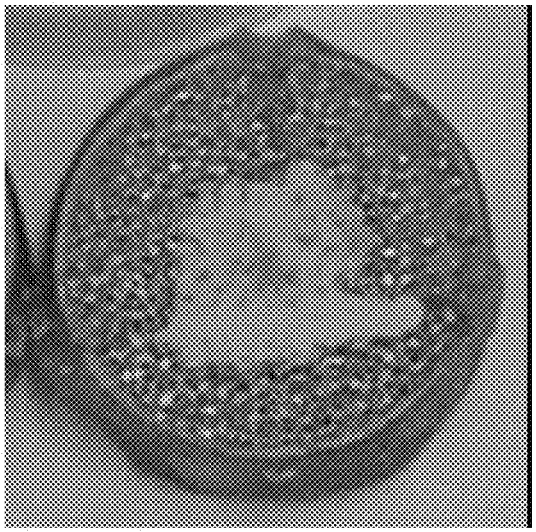
FIG. 13F is a cross-sectional view of a porous substitute sample tested under the Baroud Model for Cement II at initial injection viscosity.

Uniformity of the filling patterns quantified by the eccentricity for the Cement I groups have shown no statistically significant differences in uniformity with the increase in injection viscosity, as measured graphically in FIG. 12 and shown in FIGS. 13 A-E. Cement II had a relative low eccentricity as measured in FIG. 12 and illustrated in FIG. 13F. Statistical evaluation of the eccentricity values received from the Cement II testing samples showed significantly lower eccentricity in comparison to the Cement I groups injected at 10, 50, and 100 Pa·s, presenting a p-value of 0.005, 0.006 and 0.03, respectively. Comparison of Cement II to the Cement I group injected at 200 Pa·s resulted in a trend of reduced eccentricity for the Cement II ($p=0.079$), shown graphically in FIG. 12.

The Baroud Model was designed to favor leakage, representing a worst case cement injection. In particular, the created leakage path of 3 mm is relatively large when compared to the demonstrated diameter from vertebral veins of 0.5 to 2 mm. Furthermore, the relatively thick nature of the starch (bone marrow stimulant) makes it difficult to displace, thereby decreasing the uniformity of filling and increasing the risk of cement leakage.

Clinical observations and investigations showed less to no leakage using different commercial vertebroplasty cements, for example, Cement I: Vertecem, Synthes GmbH; and Vertebroplastic, J&J DePuy Inc., at a start injection viscosity of 50 Pa·s. Cement I injected at this viscosity level demonstrated high leakage mass under the Baroud Model, thus confirming that the Baroud Model used here favors leakage. Leaked mass observed for Cement I using starting injection viscosities below 400 Pa·s were higher than that of Cement II, and comparable to Cement II only at viscosity levels around 400 Pa·s. The biggest difference in leaked mass investigated for Cement I could be observed between 100 Pa·s and 200 Pa·s. High scattering of the parameters could be due to the model design using the 37° C. water bath.

Experimental results observed herein show a trend of reduced leakage rates and mass as starting viscosities increased for Cement I testing. These results correlate closely with the theoretical finding from the Baroud Model. Experimental results observed from Cement II showed low leakage rates in the leakage favoring Baroud Model. The experimental results demonstrate Cement II can be utilized as a bone cement and ready for injection substantially immediately after mixing and with little to no waiting phase. Cement II demonstrated a working time of at least 15 min for the entire ambient temperature range from 19-27° C., and it is applicable by using simple syringes allowing tactile feedback. Thus Cement II has an initial injectable viscosity that reduces the waiting time for commencing injection of the bone cement for example in a vertebroplasty procedure. This initial injectability, in turn reduces the risk of determining the proper injection time after mixing, e.g., too early or too late injection, and therefore increased the safety of the intervention.

To estimate the injection viscosity necessary for Cement I to demonstrate a similar leakage mass as was obtained for Cement II under the Baroud Model an extrapolation was performed A start injection viscosity for Cement I of around 600 Pa·s yielded the same amount of leaked mass as Cement II. In order to verify this phenomenological finding concerning leakage, the consistency of the cements at different viscosity levels was analyzed performing a visual inspection. The inspection of the cement consistency was performed by extruding the cement out of a 1 ml syringe. Injection steps of 0.3 ml produced a cement having a spaghetti-like appearance, as shown in FIGS. 14A-F. The cement samples were extruded from the 1 ml syringe positioned horizontally. Each injection step of 0.3 ml was about 2 sec. Cement consistency was measured by observing the lengthening of the individual cement strands due to gravitational forces.

Figure 14A:
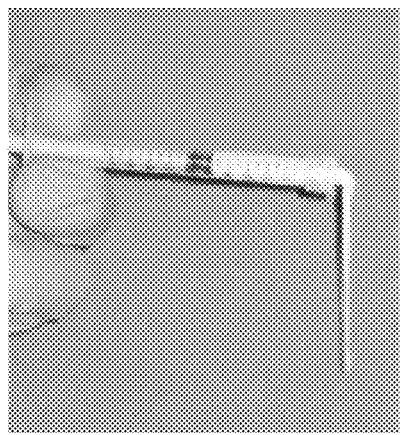
FIGS. 14A, B, C, D, E, illustrate degrees of Cement I bone cement extrusion from a syringe over a range of initial injection viscosities.
Figure 14B:
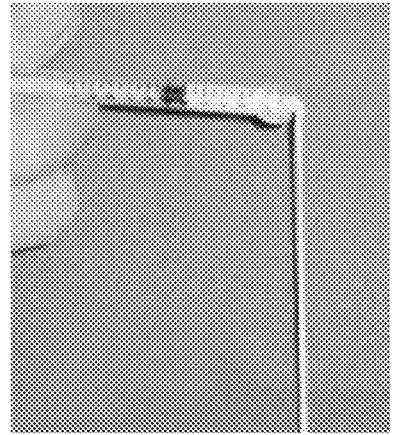
FIG. 14F illustrates Cement II bone cement extrusion from a syringe at initial injection viscosity.
Figure 14C:
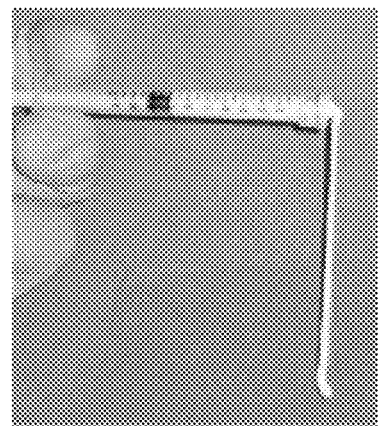
Figure 14D:
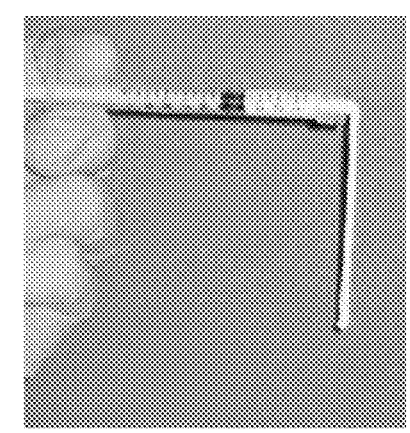
Figure 14E:
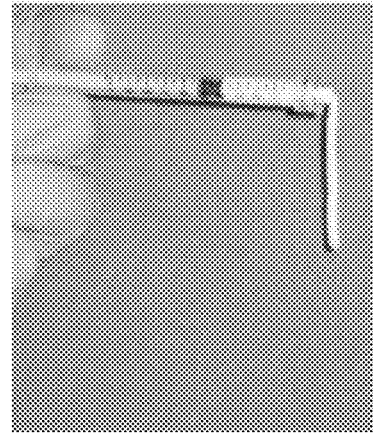
Figure 14F:
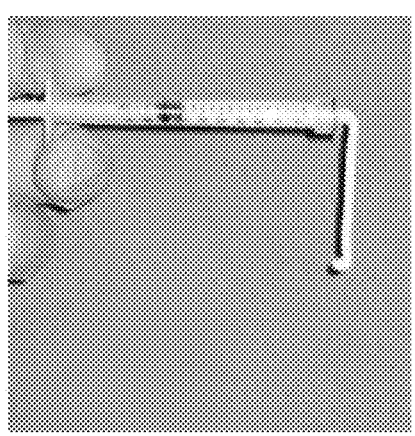

FIGS. 14A-F illustrates representative trials of the comparison of 0.3 ml cement extruded out of the syringe for six groups investigated. The visual inspection of the consistency of Cement I at a viscosity of 600 Pa·s, is shown in FIG. 14E in comparison to Cement II that was extruded immediately after preparation and having a measured viscosity of around 80 Pa·s, shown in FIG. 14F. FIGS. 14E and 14F showed a close correlation in visual inspection.

Cement I extruded having a viscosity of around 10 Pa·s, necked and lengthened right after starting extrusion followed by disruption to the strand (i.e., breaking) before the extrusion step could be finished. At a starting viscosity of around 50 Pa·s, Cement I, shown in FIG. 14A, the difference in behavior was visually in terms that the strand stayed stable longer and disrupted at the end of the injection phase. Observation while injecting Cement I having a viscosity of around 100 Pa·s, shown in FIG. 14B revealed a stable strand for about 2 sec before disruption was noticed. At 200 Pa·s shown in FIG. 14C, Cement I extrusion demonstrated a lengthening without disruption after several seconds. Lengthening rate was reduced enormously using Cement I at a viscosity of 400 Pa·s and no disruption could be observed after several seconds, as shown in FIG. 14D. As shown in FIG. 14E, Cement I having a viscosity of 600 Pa·s, and as shown in FIG. 14F Cement II as observed just after preparation, reveals a very similar behavior. A stable cement spaghetti-like strand without any noticeable lengthening was noticed for both samples after around 20 sec.

The investigation here showed that by increasing the waiting phase and thus the starting viscosity for injecting Cement I (Vertecem Synthes GmbH), the leakage mass decreased. However, Cement II showed very low leakage mass in the Baroud Model favoring leakage when applied substantially immediately after mixing. Cement II was ready to use once the solid and liquid component were mixed. As such, Cement II shortens the waiting phase for a user, e.g., physician to substantially zero minutes without compromising the safety for the procedure.

Although the present disclosure has been described in accordance with several embodiments, it should be understood that various changes, substitutions, and alterations can be made herein without departing from the spirit and scope of the present disclosure, for instance as indicated by the appended claims. Thus, it should be appreciated that the scope of the present disclosure is not intended to be limited to the particular embodiments of the process, manufacture, and composition of matter, methods and steps described herein. For instance, the various features as described above in accordance with one embodiment can be incorporated into the other embodiments unless indicated otherwise. Furthermore, as one of ordinary skill in the art will readily appreciate from the present disclosure, processes, manufacture, composition of matter, methods, or steps, presently existing or later to be developed that perform substantially the same function or achieve substantially the same result as the corresponding embodiments described herein may be utilized according to the present disclosure.

It will be appreciated by those skilled in the art that various modifications and alterations of the invention can be made without departing from the broad scope of the appended claims. Some of these have been discussed above and others will be apparent to those skilled in the art.

What is claimed is:

1. A bone cement formed by a combination of solid and liquid components comprising:
   a solid component including a contrast agent, a polymerization initiator, a calcium phosphate based bone substitute material, and a solid polymer, wherein
      the contrast agent is in a range of about 38 to about 42 percent by weight of the solid component,
      the polymerization initiator is in a range of about 0.3 to about 0.5 percent by weight of the solid component,
      the bone substitute material includes hydroxyapatite, in a range of about 14 to about 16 percent by weight of the solid component, and
      the solid polymer comprises a mixture of poly(methylacrylate-co-methylmethacrylate) and poly(methylmethacrylate) in a range of about 43 to about 46 percent by weight of the solid component, wherein the poly(methylmethacrylate) is in the range of about 3 percent to about 15 percent by weight percent of the solid polymer, and
   a liquid component including a liquid monomer, a polymerization accelerator, and optionally, a polymerization inhibitor;
   wherein the bone cement has an initial injectable viscosity suitable for manual injection onto or into a targeted anatomical location, and wherein said initial injectable viscosity being formed substantially immediately after combining the solid component and liquid component.

2. The bone cement according to claim 1, wherein:
   the mixture of poly(methylacrylate-co-methylmethacrylate) and poly(methylmethacrylate) is about 45 percent by weight of the solid polymer.

3. The bone cement according to claim 1, wherein:
   the contrast agent includes zirconium dioxide at about 40 percent by weight of the solid component.

4. The bone cement according to claim 1, wherein:
   the bone substitute material includes hydroxyapatite at about 15 percent by weight of the solid component.

5. The bone cement according to claim 1, wherein after a hardening of the cement, the bone substitute material comprises about 11 percent by weight of the hardened bone cement, the contrast agent comprises about 29 percent by weight of the hardened bone cement, and, the solid polymer comprises about 60 percent by weight of the hardened bone cement.

6. The bone cement according to claim 1, wherein the solid polymer has an average molecular weight range of about 200 kDa to about 1000 kDa.

7. The bone cement according to claim 6, wherein the solid polymer has an average molecular weight range of about 600 kDa to about 700 kDa.

8. The bone cement according to claim 7, wherein the solid polymer has an average molecular weight of substantially 600 kDa.

9. The bone cement according to claim 1, wherein the bone substitute material comprises sintered hydroxyapatite particles having an average particle diameter range of about 5 um to about 50 um.

10. The bone cement according to claim 9, wherein the bone substitute material comprises sintered hydroxyapatite particles having an average particle diameter range of about 10 um to about 30 um.

11. The bone cement according to claim 1, wherein the solid polymer comprises at least a portion of substantially spherical polymerized beads.

12. The bone cement according to claim 1, wherein the initial injectable viscosity is greater than 50 Pa·s.

13. The bone cement according to claim 1, wherein the bone cement has a waiting time of about two minutes or less.

14. The bone cement according to claim 1, wherein the bone cement has a waiting phase of about one minute or less.

15. The bone cement according to claim 1, wherein the bone cement has a waiting time of about zero minutes.

16. The bone cement according to claim 1, wherein said targeted anatomical location is one or more vertebrae.

17. The bone cement according to claim 1, wherein, after application, the bone cement displays minimal leakage.

18. A bone cement kit for treatment of a targeted anatomical location comprising:
- a first container housing a solid component, the solid component comprising contrast agent, polymerization initiator, calcium phosphate based bone substitute material, and solid polymer wherein,
    - the contrast agent is in a range of about 38 to about 42 percent by weight of the solid component,
    - the polymerization initiator is in a range of about 0.3 to about 0.5 percent by weight of the solid component,
    - the bone substitute material includes hydroxyapatite, in a range of about 14 to about 16 percent by weight of the solid component, and
    - the solid polymer comprises a mixture of poly(methylacrylate-co-methylmethacrylate) and poly(methylmethacrylate) in a range of about 43 to about 46 percent by weight of the solid component, wherein the poly(methylmethacrylate) is in the range of about 3 percent to about 15 percent by weight percent of the solid polymer,
- a second container containing a liquid component, the liquid component comprising liquid monomer, polymerization accelerator, and optionally polymerization inhibitor; wherein the solid component and liquid component are combinable to form a bone cement having an initial viscosity suitable for manual injection onto or into a targeted anatomical location with minimal leakage, and
- optionally one or more syringes adapted to inject the bone cement.

19. The bone cement kit according to claim 18 wherein said targeted anatomical location is one or more vertebrae.

20. A method for preparing the bone cement composition of claim 1, said method comprising the steps of:
- filling a first container with the solid component;
- filling a second container with the liquid component; and
- combining the liquid component and the solid component using a mixer.

21. A method for treating a targeted anatomical location with a bone cement comprising the step of manually injecting or applying the bone cement of claim 1 onto or into the targeted anatomical location.

22. The method of claim 21, wherein the step of manually injecting includes manual actuation of a first syringe that produces a hydraulic pressure to effect the injection or application of the cement housed in a second syringe.

23. The method of claim 21 wherein the targeting anatomical location is one or more vertebrae.

24. A method for augmenting, replacing or treating, weakened or collapsed vertebrae using bone cement, said method comprising the step of manually injecting the bone cement of claim 1 onto or into one or more vertebrae.

25. The method of claim 24, wherein the step of manually injecting includes manual actuation of a first syringe that produces a hydraulic pressure to effect the injection or application of the cement housed in a second syringe.

* * * * *